United States Patent [19]

Cocco

[11] Patent Number: 4,827,027

[45] Date of Patent: May 2, 1989

[54] SEPARATION/PURIFICATION OF SALICYCLIC ACID

[75] Inventor: Roger Cocco, Saint-Symphorien d'Ozon, France

[73] Assignee: Rhone-Poulenc Specialites Chimiques, Courbevoie, France

[21] Appl. No.: 924,424

[22] Filed: Oct. 29, 1986

[30] Foreign Application Priority Data

Oct. 29, 1985 [FR] France .................. 85 16259

[51] Int. Cl.$^4$ .............................................. C07G 65/10
[52] U.S. Cl. .................................................. 562/477
[58] Field of Search ......................................... 562/477

[56] References Cited

FOREIGN PATENT DOCUMENTS 1061806  4/1954  France .
1539528  9/1968  France .
1174190 12/1969  United Kingdom ................ 562/477

*Primary Examiner*—Paul J. Killos
*Attorney, Agent, or Firm*—Burns, Doane, Swecker & Mathis

[57] ABSTRACT

Essentially pure salicylic acid crystals, typically containing less than 0.01% inorganic salt, less than 0.01% para-hydroxybenzoic and 4-hydroxyisophthalic acid and well adopted for foodstuff and pharmaceutical applications, are facilely recovered from an aqueous solution of sodium salicylate by (i) adding an organic solvent for salicylic acid to such aqueous solution, in an amount sufficient to dissolve the salicylic acid corresponding to said sodium salt thereof, (ii) next adding thereto an at least stoichiometric amount, relative to said sodium salicylate, of a strong inorganic acid, and (iii) separating therefrom an essentially organic phase which comprises said salicylic acid and an aqueous phase which comprises an inorganic sodium salt.

11 Claims, No Drawings

SEPARATION/PURIFICATION OF SALICYCLIC ACID

CROSS-REFERENCE TO RELATED APPLICATION

Copending application, Ser. No. 924,427, filed concurrently herewith and assigned to the assignee hereof.

BACKGROUND OF THE INVENTION

1. Field of the Invention:

The present invention relates to the separation and purification of salicylic acid, and, more especially, to the precipitation of salicylic acid from its sodium salt and the purification thereof.

2. Description of the Prior Art:

Salicylic acid is conventionally prepared by carboxylating sodium phenate wih carbon dioxide, under a pressure generally greater than 50 bars and at a temperature on the order of 150° C. to 160° C. Compare French Pat. No. 1,122,915, for example.

The sodium phenate is preferably employed in suspension in free phenol, for example, in a ratio by weight of phenol/sodium phenate of 3/1 to 5/1.

When the reaction is complete, the reaction mass is treated in order to separate therefrom the sodium salts of product hydroxybenzoic and hydroxyphthalic acids, which are essentially monosodium salicylate, possibly disodium salicylate and, in much smaller proportions, sodium parahydroxybenzoate and sodium 4-hydroxyisophthalate in this case.

The sodium salicylates obtained by the processes of carboxylation of sodium phenate are generally monosodium salicylate (monosodium 2-hydroxybenzoate), possibly containing some disodium salicylate. In the description that follows, except where otherwise indicated, the term "sodium salicylate" will refer more particularly to monosodium salicylate, possibly containing some disodium salicylate, but it will be understood that the process of the invention is not limited to the monosodium salt alone and can be applied equally as well to disodium salicylate, or to mixtures of monosodium and disodium salts principally comprising the disodium salt.

This treatment may especially include addition of water, which dissolves the sodium salt of hydroxybenzoic and hydroxyphthalic acids, and a liquid/liquid extraction step using a water-immiscible solvent. Such an operation thus provides an organic solution especially containing free phenol and an aqueous solution containing the sodium salts mentioned above.

Serious need thus exists in this art for the improved precipitation and purification of salicylic acid from such aqueous solutions.

Indeed, the treatment of aqueous solutions of sodium salicylate typically includes precipitating salicylic acid and the other organic acids with a strong inorganic acid, and especially with sulfuric acid. This treatment requires a large excess of the strong inorganic acid and several successive washings with water in order to remove the maximum of the salt formed (most frequently, sodium sulfate). The salicylic acid obtained may then be crystallized once, or several times, to reduce the level of other organic acids contained therein.

The salicylic acid obtained by the usual process contains amounts of sodium sulfate, and to a lesser extent, para-hydroxybenzoic acid and 4-hydroxyisophthalic acid, which are still too high for certain applications of salicylic acid in the food industry or in medicine.

SUMMARY OF THE INVENTION

Accordingly, a major object of the present invention is the provision of an improved process for the separation/purification of salicylic acid, which improved process enables the simple production of a salicylic acid of sufficient purity for common end uses, or the production of a salicylic acid of very high purity, also by way of a process far simpler than those of the prior art.

Briefly, the present invention features a process for the precipitation and purification of salicylic acid from an aqueous solution of sodium salicylate, comprising the following sequence of stages:

1. addition to said aqueous solution of an organic solvent of salicylic acid, in an amount sufficient to dissolve the salicylic acid corresponding to the sodium salt employed;
2. addition of a strong inorganic acid in an amount at least equal to the stoichiometric amount relative to the sodium salicylate;
3. separation of an essentially organic phase containing salicylic acid and of an aqueous phase containing the inorganic sodium salt formed.

DETAILED DESCRIPTION OF THE PREFERRED EMBODIMENTS OF THE INVENTION

More particularly according to the present invention, any acid capable of releasing salicylic acid from its salt can be used as the strong inorganic acid; sulfuric acid, hydrochloric acid and phosphoric acid are representative. Because of cost or lower corrosion factors, it is generally preferred to use sulfuric acid. In the description of the process of the invention that follows, acidification by sulfuric acid will therefore most frequently be referred to for convenience, but this does not exclude the use of other strong inorganic acids.

The organic solvents which are suitable for carrying out the process according to the invention are solvents in which salicylic acid is soluble, whereas the inorganic sodium salt is insoluble, or only slightly soluble.

Representative are aliphatic ethers, substituted aliphatic ethers, aliphatic ketones, halogenated aliphatic ketones, aliphatic aldehydes, and aliphatic alcohols.

For practical and economic reasons, it is not desirable to use organic solvents which have a very high boiling point, as the solvent will generally be removed by distillation during the isolation of the salicylic acid, and, upon completion of purification, the salicylic acid must contain the least possible trace amounts of the solvent used.

Thus, a solvent having a boiling point less than or equal to 120° C. and, even more particularly, less than or equal to 100° C., will be preferred.

Exemplary of such solvents, the following are representative:

aliphatic ethers, such as diisopropyl ether; methyl tert-butyl ether; ethyl isopropyl ether, ethyl propyl ether; butyl ethyl ether; ethyl isobutyl ether; ethyl tert-butyl ether; butyl methyl ether; isobutyl methyl ether; methyl pentyl ether; diethyl ether; dipropyl ether; isopropyl propyl ether; ethyl 1-propynyl ether; ethyl 2propynyl ether; ethynyl propyl ether; allyl ethyl ether; allyl isopropyl ether; isopropyl vinyl ether or isobutyl vinyl ether;

halogenated aliphatic ethers, such as 2-bromoethyl ethyl ether; 2-chloroethyl ethyl ether;

aliphatic ketones, such as acetone; 2-butanone; 3-methyl-2-butanone; 3,3-dimethyl-2-butanone; 2-pentano 3-pentanone;

chlorinated aliphatic ketones, such as 3-chloro-2butanone or 1-chloro-2-propanone;

aliphatic aldehydes, such as propanal; butanal; 2methylbutanal; 3-methylbutanal; pentanal; methoxyethanal or ethoxyethanal;

chlorinated aliphatic aldehydes, such as chloroethanal; dichloroethanal; 2-chloropropanal or 2-chloro-2-methylpropanal;

aliphatic alcohols, such as methanol; ethanol; isopropanol; n-propanol, n-butanol; isobutanol or tert-butanol.

Among the solvents advantageously used in the process according to the invention, the aliphatic ethers, chlorinated aliphatic ethers, aliphatic ketones and chlorinated aliphatic ketones are more particularly preferred.

The amount of organic solvent used may vary over very wide limits.

The lower limit is established by the solubility of salicylic acid in the solvent at the temperature at which the reaction is carried out.

The upper limit is generally non-critical, but it will be appreciated that, from an economic point of view, it is not profitable to operate at very low final concentrations of salicylic acid in the solvent.

Additionally, when the organic solvent is miscible with water, it is essential that the final concentration of salicylic acid in the solvent be adequate, such that a separation occurs between an aqueous layer containing the inorganic sodium salt formed and an essentially organic layer containing salicylic acid.

For these reasons, the amount of solvent is such that the final salicylic acid concentration in said solvent is generally at least equal to 8% by weight.

The temperature at which the process according to the invention is carried out is not very critical. It usually ranges from 10° C. to the boiling point of the organic solvent used.

However, as far as possible, it is preferred to avoid very low temperatures which may, especially, give rise to a crystallization of the inorganic sodium salt, or also very high temperatures, at which the solubility of salicylic acid in water is increased.

Accordingly, the reaction is preferably carried out at temperatures of from 40° C. to 80° C., this range not being critical.

The amount of strong inorganic acid and, more particularly, of sulfuric acid used is generally slightly greater than the amount theoretically required to release the salicylic acid and the para-hydroxybenzoic and 4-hydroxyisophthalic acids from their respective sodium salts.

This excess, which is often approximately 5% to 10% of the stoichiometric amount, enables the reaction to be completed more rapidly.

The sulfuric acid is advantageously introduced in the form of an aqueous solution, such as those commercially available; aqueous solutions which have a concentration of 60% to 98% by weight are most frequently used.

In practice, the process according to the present invention may be carried out as follows:

(i) An organic solvent as defined above, in an amount sufficient to dissolve salicylic acid corresponding to the sodium salicylate used, is added to the aqueous solution containing sodium salicylate at a concentration of 20 to 45% by weight and, where appropriate, sodium salts of other acids;

(ii) A homogeneous phase or two liquid phases are obtained, depending upon the circumstances;

(iii) Sulfuric acid is then added, under stirring, in an amount representing approximately 105% to 110% of the amount theoretically required (theory being 0.5 mole of pure $H_2SO_4$ for 1 mole of monosodium salicylate, or of sodium para-hydroxybenzoate, and 1 mole of $H_2SO_4$ for 1 mole of disodium salicylate, or from 1 mole of sodium 4-hydroxyisophthalate);

(iv) The temperature is adjusted to the required value.

When the reaction is complete, two liquid phases are obtained:

(a) an aqueous phase containing practically all of the sodium sulfate formed, and very little salicylic acid;

(b) an essentially organic phase containing almost all of the salicylic acid formed.

In effect:

either a solvent which is immiscible with water and consequently settles has been employed;

or a solvent miscible with water has been employed, and separation occurs between the aqueous phase containing sodium sulfate and the organic phase containing the salicylic acid.

The separation of these two phases is then carried out by decantation. The aqueous phase generally contains more than 20% by weight of sodium sulfate (which may, if required, be recovered) and less than 0.5% by weight of salicylic acid (generally less than 0.1% by weight of salicylic acid, when one of the preferred organic solvents is used).

The essentially organic phase is then treated in a manner known, per se, in order to separate the salicylic acid.

For example, if the intended applications do not require a much greater purity than that obtained in the usual processes for the separation of salicylic acid, an atomization of the said organic phase, that is, spraying it through a nozzle at a temperature which permits the instantaneous vaporization of the solvent, may be carried out. This process is simple and provides a salicylic acid of a purity at least comparable to that obtained by the processes of the prior art.

It is also possible to carry out a distillation of the organic solvent, followed by a cooling and a crystallization of the salicylic acid by the addition of water, this typically being the preferred embodiment.

The salicylic acid obtained according to this latter embodiment has a very low sodium sulfate content generally less than 0.01% by weight and, when the preferred organic solvents are used, less than 0.002% by weight, and a para-hydroxybenzoic acid and 4-hydroxyisophthalic acid content generally less than 0.01% and, when one of the preferred organic solvents is used, less than 0.005% by weight.

Such a salicylic acid may be used for the most stringent of applications in the food and pharmaceutical industries.

Additionally, it is observed that the salicylic acid crystals thus prepared have a particle size which may be controlled during crystallization by adjusting the temperature at which this operation is carried out. Thicker needles and a higher bulk density, resulting in a clear improvement in the flowability of the salicylic acid, are obtained.

The process of the invention may be carried out in a discontinuous or a continuous manner. It can easily be carried out within the context of the usual processes for the preparation of salicylic acid from sodium phenate.

In order to further illustrate the present invention and the advantages thereof, the following specific examples are given, it being understood that same are intended only as illustrative and in nowise limitative.

EXAMPLE 1

750 g of an aqueous solution at a concentration of 39.7% by weight of sodium salicylate (1.87 mole), containing organic impurities (sodium salts of parahydroxyisophthalic acid and of para-hydroxybenzoic acid, in a total amount corresponding approximately to 1% of the weight of sodium salicylate), followed by 600 g of acetone, were charged into a 2.5-liter glass reactor equipped with an efficient stirrer. The contents of the reactor were stirred and 141 g of a 71% by weight aqueous solution of sulfuric acid (1.02 mole of $H_2SO_4$) were added over the course of 30 minutes.

Stirring was carried out for 30 minutes, increasing the temperature to 55° C. at the same time.

The contents of the reactor were then allowed to settle for 30 minutes at approximately 55° C.; two phases were obtained:

(a) a lower aqueous phase; and
(b) an upper organic phase.

The aqueous phase was drawn off, which was still at a temperature of about 55° C.

This aqueous phase contained:
(i) approximately 338 g of water;
(ii) approximately 6 g of acetone;
(iii) 136.3 g of sodium sulfate and sulfuric acid;
(iv) approximately 2 g of salicylic acid.

The acetone phase contained:
(i) 456 g of acetone;
(ii) 162 g of water;
(iii) 256.0 g of salicylic acid (amount determined);
(iv) 2.4 g of para-hydroxybenzoic acid;
(v) 0.4 g of 4-hydroxyisophthalic acid;
(vi) 0.2 g of sodium sulfate.

The organic phase was treated in the following manner:

the acetone was distilled, while maintaining the volume of the phase constant by the gradual addition of water;

the distillation was terminated when the temperature of the condenser was at 98° C–100° C.

A new aqueous phase containing salicylic acid crystals in suspension was thereby obtained.

This suspension was cooled from 100° C. to 85° C. over two hours, then from 85° C. to 40° C. over one hour.

The salicylic acid which had crystallized was filtered at 40° C. The salicylic acid was washed with approximately 400 g of water, and it was then dried.

248 g of salicylic acid in the form of a crystallized white solid, having good flowability, were obtained.

The salicylic acid contained, as impurities:
(1) approximately 0.005% of para-hydroxybenzoic acid;
(2) approximately 0.001% of 4-hydroxyisophthalic acid;
(3) approximately 0.001% of sodium sulfate.

The yield of isolation and of purification of the salicylic acid, relative to the sodium salicylate used, was approximately 96%.

The yield may be further improved by treatment of the aqueous phase.

EXAMPLE 2

The reaction was carried out as in Example 1, but with lesser amounts of charges in a 500-cm$^3$ glass reactor and using diisopropyl ether as the solvent.

The following charges were used:
(i) 126 g of an aqueous solution containing 30 g of sodium salicylate;
(ii) 65.5 g of diisopropyl ether;
(iii) 11.2 g of 95% sulfuric acid.

After the different stages in the procedure described in Example 1, the following were obtained:
(a) 109 g of aqueous phase;
(b) 89.6 g of organic phase containing 25.5 g of salicylic acid. By treating the organic phase as indicated in Example 1, 25.1 g of salicylic acid containing 0.0003% of sodium sulfate (97% yield relative to the sodium salicylate used).

EXAMPLE 3

The reaction was carried out as in Example 1, but using lesser amounts of charges in a 500-cm$^3$ reactor and using ethanol as the solvent.

The following charges were used:
(i) 126 g of an aqueous solution containing 30 g of sodium salicylate;
(ii) 65 g of ethanol;
(iii) 11 g of 95% sulfuric acid.

After the different stages in the procedure described in Example 1, the following were obtained;
(a) 41 g of aqueous phase;
(b) 158.4 g of organic phase (which contained more water than in Example 2) containing 25.0 g of salicylic acid and 1.8 g of sodium sulfate. By treating the organic phase as indicated in Example 1, 24.5 g of salicylic acid containing 0.01 g of sodium sulfate (94% yield relative to the sodium salicylate used) were obtained.

A less efficient separation of the aqueous and organic phases was observed with ethanol, because of which a larger amount of sodium sulfate was determined in the salicylic acid obtained.

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the recovery of purified salicylic acid from an aqueous solution of sodium salicylate, comprising (i) adding an organic solvent for salicylic acid to such aqueous solution, in an amount sufficient to dissolve the salicylic acid corresponding to said sodium salt thereof, said organic solvent having a boiling point less than or equal to 120° C., (ii) next adding thereto an at least stoichiometric amount, relative to said sodium salicylate, of a strong inorganic acid, and (iii) separating therefrom an essentially organic phase which comprises said salicylic acid and an aqueous phase which comprises an inorganic sodium salt.

2. The process as defined by claim 1, further comprising crystallizing salicylic acid from said organic phase.

3. The process as defined by claim 1, said strong inorganic acid comprising sulfuric acid.

4. The process as defined by claim 1, said organic solvent comprising an aliphatic ether, substituted aliphatic ether, aliphatic ketone, halogenated aliphatic ketone, aliphatic aldehyde or aliphatic alcohol.

5. The process as defined by claim 4, said organic solvent comprising an aliphatic ether, chlorinated aliphatic ether, aliphatic ketone or chlorinated aliphatic ketone.

6. The process as defined by claim 1, said organic solvent comprising diisopropyl ether, methyl tert-butyl ether, ethyl isopropyl ether, ethyl propyl ether, butyl ethyl ether, ethyl isobutyl ether, ethyl tert-butyl ether, butyl methyl ether, isobutyl methyl ether, methyl pentyl ether, diethyl ether, dipropyl ether, isopropyl propyl ether, ethyl 1-propynyl ether, ethyl 2-propynyl ether, ethynyl propyl ether, allyl ethyl ether, allyl isopropyl ether, isopropyl vinyl ether, isobutyl vinyl ether, 2-bromoethyl ethyl ether, 2-chloroethyl ethyl ether, acetone, 2-butanone, 3-methyl-2-butanone, 3,3-dimethyl-2butanone, 2-pentanone, 3-pentanone, 3-chloro-2-butanone, or 1-chloro-2-propanone.

7. The process as defined by claim 1, wherein the amount of organic solvent added is such that the final salicylic acid concentration in said solvent is at least equal to 8% by weight.

8. The process as defined by claim 1, carried out at a temperature of from 10° C. to the boiling point of said organic solvent.

9. The process as defined by claim 1, comprising adding from about 105% to 110% of the stoichiometric amount of sulfuric acid.

10. An essentially pure salicylic acid containing less than 0.01% by weight of sodium sulfate and less than 0.01% by weight of para-hydroxybenzoic acid and 4-hydroxyisophthalic acid.

11. The essentially pure salicylic acid as defined by claim 10, containing less than 0.002% by weight of sodium sulfate and less than 0.005% by weight of para-hydroxybenzoic acid and 4-hydroxyisophthalic acid.

* * * * *